United States Patent
Li et al.

(10) Patent No.: US 9,410,975 B2
(45) Date of Patent: Aug. 9, 2016

(54) PRESSURE MANIFOLD TO EQUALIZE PRESSURE IN INTEGRATION PCR-CE MICROFLUIDIC DEVICES

(75) Inventors: Chen Li, Santa Clara, CA (US); Samuel Chan, Daly City, CA (US); Jian Ping Zhang, Moraga, CA (US)

(73) Assignee: AEL MINING SERVICES LIMITED, Woodmead (ZA)

( * ) Notice: Subject to any disclaimer, the term of this patent is extended or adjusted under 35 U.S.C. 154(b) by 410 days.

(21) Appl. No.: 12/600,171

(22) PCT Filed: May 15, 2008

(86) PCT No.: PCT/US2008/006266
§ 371 (c)(1),
(2), (4) Date: Mar. 29, 2010

(87) PCT Pub. No.: WO2008/143959
PCT Pub. Date: Nov. 27, 2008

(65) Prior Publication Data
US 2010/0200402 A1 Aug. 12, 2010

Related U.S. Application Data

(60) Provisional application No. 60/938,171, filed on May 15, 2007.

(51) Int. Cl.
*B01L 3/00* (2006.01)
*G01N 27/26* (2006.01)
*G01N 35/10* (2006.01)
*C12P 19/34* (2006.01)
*G01N 35/00* (2006.01)

(52) U.S. Cl.
CPC ...... *G01N 35/1095* (2013.01); *B01L 3/502715* (2013.01); *B01L 3/50273* (2013.01); *B01L 3/502707* (2013.01); *B01L 3/502723* (2013.01); *B01L 2200/027* (2013.01); *B01L 2200/0684* (2013.01); *B01L 2300/0645* (2013.01); *B01L 2300/0819* (2013.01); *B01L 2400/049* (2013.01); *B01L 2400/0487* (2013.01); *G01N 2035/00158* (2013.01); *G01N 2035/00237* (2013.01)

(58) Field of Classification Search
CPC .......... B01L 2200/027; B01L 2200/0684; B01L 2300/0645; B01L 2300/0819; B01L 2400/0487; B01L 2400/049; B01L 3/502715; G01N 2035/00158; G01N 2035/00237; G01N 35/1095

See application file for complete search history.

(56) References Cited

U.S. PATENT DOCUMENTS

| | | | |
|---|---|---|---|
| 6,915,679 B2 * | 7/2005 | Chien et al. | 73/54.01 |
| 7,033,840 B1 * | 4/2006 | Tagge et al. | 436/147 |
| 7,223,363 B2 * | 5/2007 | McNeely et al. | 422/417 |
| 7,607,641 B1 * | 10/2009 | Yuan | 251/331 |
| 2002/0068357 A1 * | 6/2002 | Mathies et al. | 435/287.2 |
| 2004/0126279 A1 * | 7/2004 | Renzi et al. | 422/100 |
| 2005/0095602 A1 * | 5/2005 | West et al. | 435/6 |
| 2005/0255007 A1 * | 11/2005 | Yamada et al. | 422/100 |
| 2006/0063160 A1 * | 3/2006 | West et al. | 435/6 |
| 2006/0211134 A1 * | 9/2006 | Kennedy et al. | 436/180 |
| 2006/0258019 A1 * | 11/2006 | Chow et al. | 436/180 |

* cited by examiner

*Primary Examiner* — Jennifer Wecker
(74) *Attorney, Agent, or Firm* — Finnegan, Henderson, Farabow, Garrett & Dunner LLP

(57) ABSTRACT

A device is presented that includes a chip having a plurality of wells that are optionally connected by capillary channels, and a manifold member configured to be disposed over the chip for equalizing pressure over the wells and capillary channels.

18 Claims, 11 Drawing Sheets

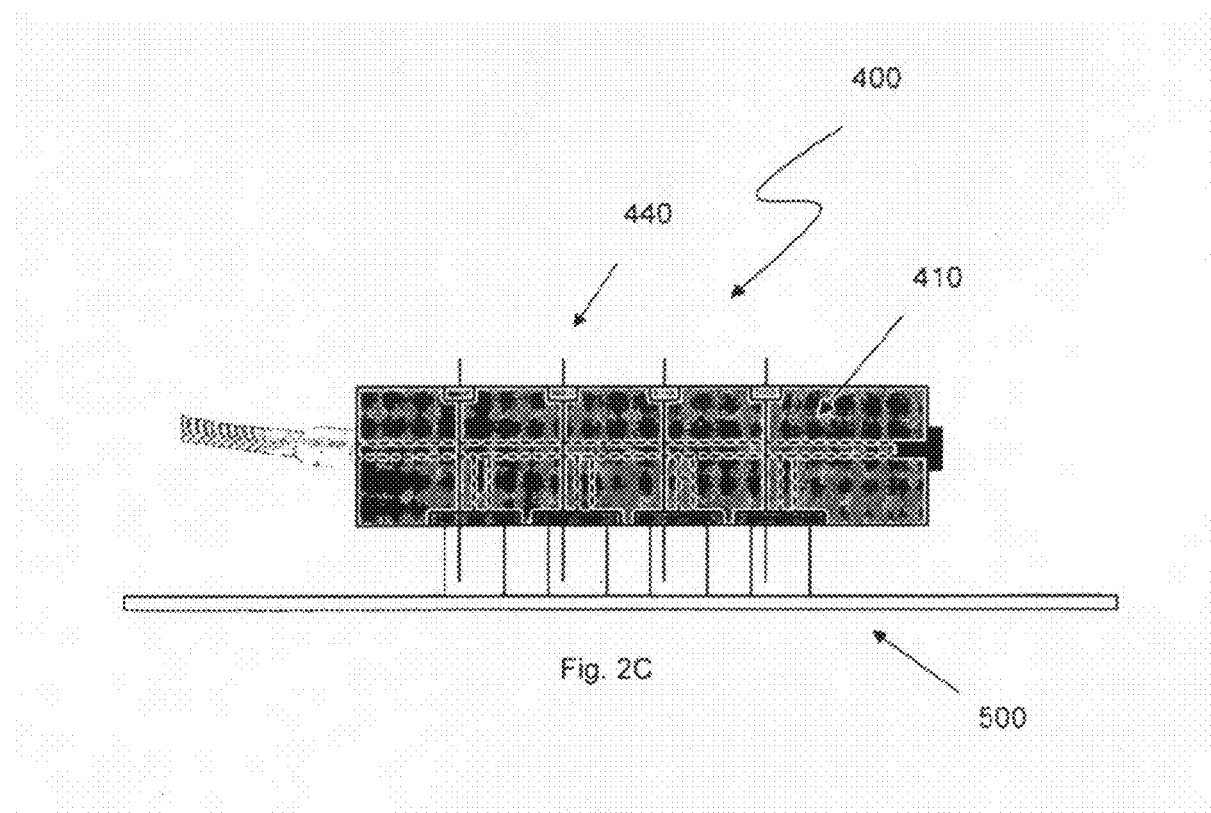

PRESSURE MANIFOLD TO EQUALIZE PRESSURE IN INTEGRATION PCR-CE MICROFLUIDIC DEVICES

RELATED APPLICATION

This application is the national stage of International Application No. PCT/US2008/006266, filed May 15, 2008, which claims the benefit of U.S. Provisional Application No. 60/938,171, filed May 15, 2007, which is incorporated herein by reference.

FIELD OF THE INVENTION

The present invention relates to a device that includes a chip having a plurality of wells that are optionally connected by capillary channels, and a manifold member configured to be disposed over the chip for equalizing pressure over the wells and capillary channels to prevent evaporation, condensation, and unintended movement of liquid in the wells and channels.

BACKGROUND OF THE INVENTION

Microfluidic PCR has evolved since Wilding and coworkers first performed PCR in a chamber in a microchip device (Wilding, P., Shoffner, M. A., Kricka, L. J., *PCR in a silicon microstructure*, Clin. Chem., 1994, 40, 1815-1818). Northrup et al. described a device that coupled a PCR reactor and a capillary electrophoresis (CE) module fabricated on different substrates (Woolley, A. T., Hadley, D., Landre, P I, deMello A. J., Mathies, R. A., Northrup, M. A. *Functional integration of PCR amplification and capillary electrophoresis in a microfabricated DNA analysis device*, Anal. Chem., 1996, 68, 4081-4086). Later, Burns' group developed an integrated device which could perform PCR and gel-based electrophoresis (Burns, M. A., Johnson, B. N., Brahmasandra, S. N., Handique, K, Webster, J. R., Krishnan, M., Sammarco, T. S., Man, P. M., Jones, D., Heldsinger, D., Mastrangelo, C. H., Burke, D. T., *An integrated nanoliter DNA analysis device*, Science, 1998, 282, 484-487). Lagally from Mathies group and Koh from ACLARA Biosciences also demonstrated PCR-CE in integrated microfluidic devices (Lagally, E. T., Simpson, P. C., Mathies, R. A., *Monolithic integrated microfluidic DNA amplification and capillary electrophoresis analysis system*, Sensors and Actuators B, 2000, 63, 138-146; and Koh, C. G., Tan, W., Zhao, M., Ricco, A. J., Fan, Z. H., *Integrating polymerase chain reaction, valving, and electrophoresis in a plastic device for bacterial detection*, Anal. Chem., 2003, 75, 4591-4598). Hess et al. used a reactor to carry out PCR under high pressures to control nucleic acid hybridization (Hess, R. S., Laugharn, J. A. Jr., Green, D. J., Pressure-controlled nucleic acid hybridization, U.S. Pat. No. 6,753,169B2, Jun. 22, 2004).

The temperature needed to conduct PCR can reach up to 95° C., which is close to the boiling point of water. At such a high temperature, evaporation is severe and it can change the concentration in the reaction solution and lower the PCR efficiency. Bubbles can be generated inside the solution in the PCR chamber, generating pressure differences in microfluidic channels and pushing liquid out of intended regions; for example, a separation buffer can be moved out of a CE separation channel. Further, the valves, such as gel valves, wax valves, and hydrophobic material generally used in many of the microfluidic devices are not reusable, limiting the devices to the detection of PCR amplification only at the final phase or at the end-point of the PCR reaction.

Disposable PCR devices are desirable to avoid carryover and cross-contamination issues. Moreover, although valves can be used to prevent evaporation and liquid movement, incorporation of valves into microfluidic PCR devices will substantially increase the cost of fabrication. Use of valves in microfluidic PCR systems is also questionable because they tend to lose their functions once they are activated and, consequently, do not allow continuous or multiple sampling of products from the reaction chamber.

A device is presented with a manifold used to suppress or prevent evaporation, condensation, and unintended movement of liquid because of pressure differences, for example, in a microfluidic channel network during PCR cycles.

SUMMARY OF THE INVENTION

A device is presented that includes a chip having a plurality of wells that are optionally connected by capillary channels, and a manifold member configured to be disposed over the chip for equalizing pressure over the wells and capillary channels.

The manifold member may be placed over a polymerase chain reaction (PCR) capillary electrophoresis (CE) chip to suppress or prevent evaporation, condensation, and unintended movement of liquid therein because of pressure differences in the wells and chip channels during PCR cycles.

It is to be understood that both the foregoing general description and the following detailed description are exemplary and explanatory only and are not restrictive of the invention, as claimed. Although the embodiments described below are directed to the use of the device with microfluidic PCR-CE chips, the device itself is not limited to its use with such chips.

The accompanying drawings, which are incorporated in and constitute a part of this specification, illustrate embodiments of the invention and together with the description, serve to explain the principles of the invention. When the same numeral references are used between drawings, they refer to the same or similar elements. Furthermore, any and all references described in this disclosure are all incorporated herein by reference.

BRIEF DESCRIPTION OF THE DRAWINGS

FIGS. 2A, 2B and 2C are embodiments of a device of the present invention.

DESCRIPTION OF THE EMBODIMENTS

Reference will now be made in detail to the exemplary embodiments of the invention, examples of which are illustrated in the accompanying drawings. Wherever possible, the same reference numbers will be used throughout the drawings to refer to the same or like parts.

An embodiment of the invention described here is a manifold used in microfluidic devices to suppress or prevent evaporation, condensation and unintended movement of liquid because of pressure differences in microfluidic channels during PCR cycles. The manifold allows the wells and the microfluidic channels of the microfluidic device to be sealed off from the external environment, so that no pressure differences can build up during PCR cycling. It also allows an external pressure source to be connected to all the wells. The application of the external pressure raises the boiling point of the PCR solution so that evaporation during thermal cycling can be suppressed.

Figure 1:
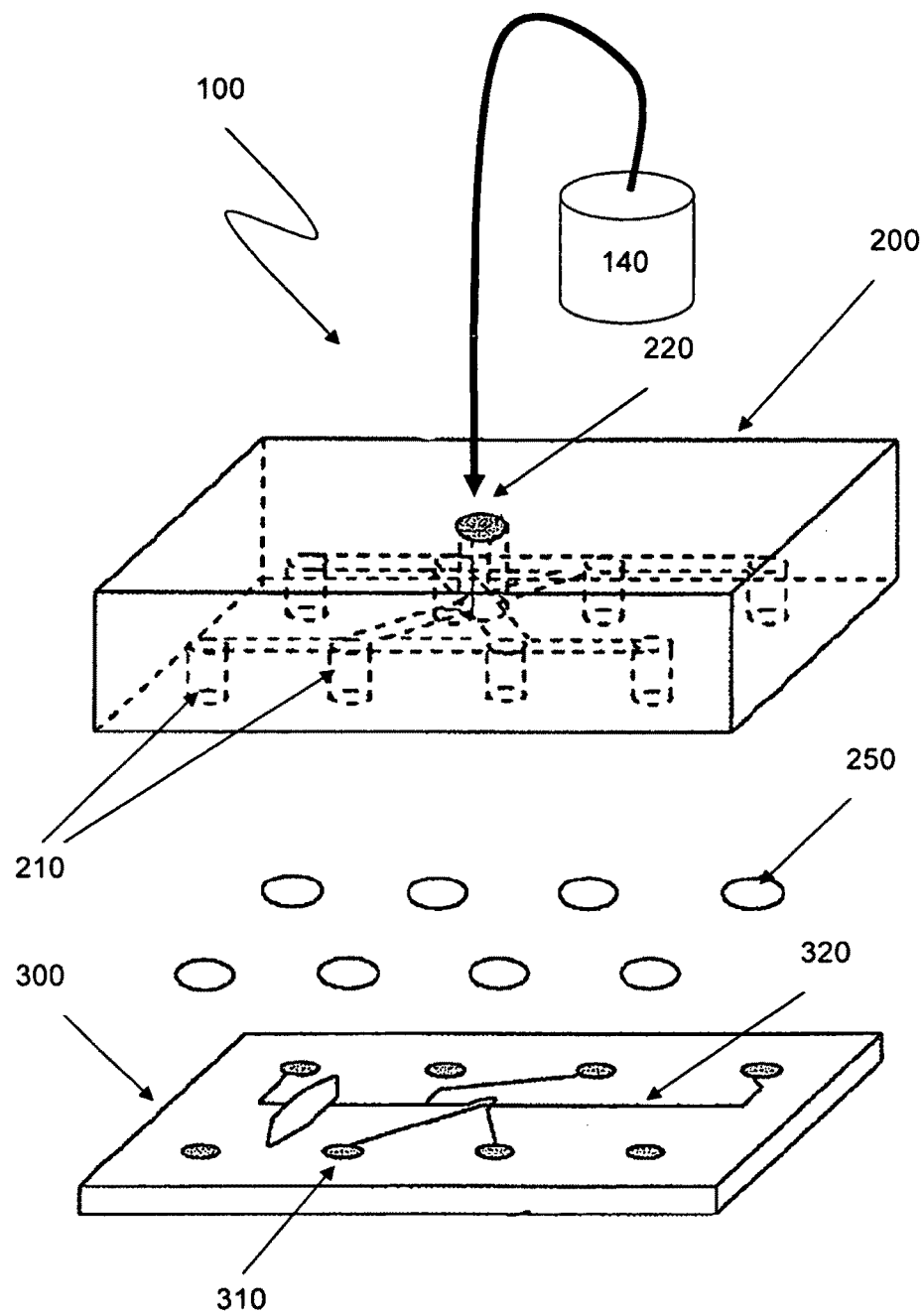
FIG. 1 is an embodiment of a device of the present invention.

An embodiment of the present invention is shown in FIG. 1. A microfluidic device 100 includes a manifold block 200 and a microfluidic PCR-CE chip 300. The manifold block 200 has interconnecting channels 210, which can interface with each well in the microfluidic PCR-CE chip 300. It also has an external pressure port 220 on top of the manifold block 200. The manifold block 200 can have more than one external pressure port, and a group of interconnecting channels may lead to one port while another group of channels can lead to another port. The PCR-CE chip 300 is shown with a total of eight wells 310 interconnected by channels 320 but the chip can have more or fewer wells depending on the need, and the channels can be accordingly arranged. The channels 320 may originate from the bottom of the wells 310 and extend within the chip 300. The size of each well may be uniform or different from another depending on the application. Gaskets 250 such as O-rings are sandwiched between the manifold block 200 and the PCR-CE microfluidic chip 300. The manifold block 200, the gaskets 250, and the PCR-CE microfluidic chip 300 are clamped together to seal the wells 310 and channels 320 from the external environment. A regulated external pressure from an external pressure source 140 can be applied through the port 220 on the top of the manifold block 200. The manifold block 200 serves to equalize the pressure differences generated by gas or vapor in the microfluidic device 100. Pressure of 100 psi or less and 10 psi or above can be used to control solution evaporation at elevated incubation temperature in the microfluidic device 100. The pressure may be about 20 psi to 40 psi, and may further be between about 30 psi to 40 psi. However, the pressure is not limited to 100 psi and less. The upper limit of pressure may be higher depending on the need for greater pressure, for example to further lower the boiling point of the solution.

In PCR, temperatures can go up to 95° C. during a denaturation step. At around that temperature, evaporation can occur and bubbles can be generated. In microfluidic devices, these changes can lead to generation of large pressure differences between different compartments and channels and can result in uncontrollable evaporation, condensation, and unintended movement of liquid.

Figure 2A:
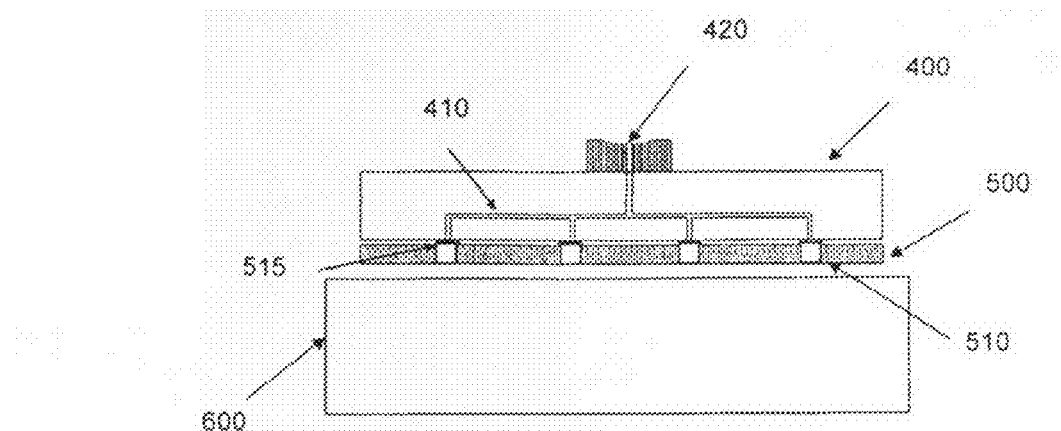

In another exemplary embodiment of the present invention, a manifold block 400 shown in a cross-sectional view in FIG. 2A was made of acrylic plastic. The manifold block 400 was designed to be disposed over a microfluidic PCR-CE chip 500 with a total of eight wells 510, which are overlaid with O-rings 515 (only four seen from the side view) to seal the wells, but the number of wells may be changed according to the need. The interconnecting channels 410 disposed within the manifold block 400 were configured to interface at their ends with each of the wells 510 on the PCR chip 500. The interconnecting channels 410 come together to an external port 420 that leads to an external pressure source (not shown).

Figure 2B:
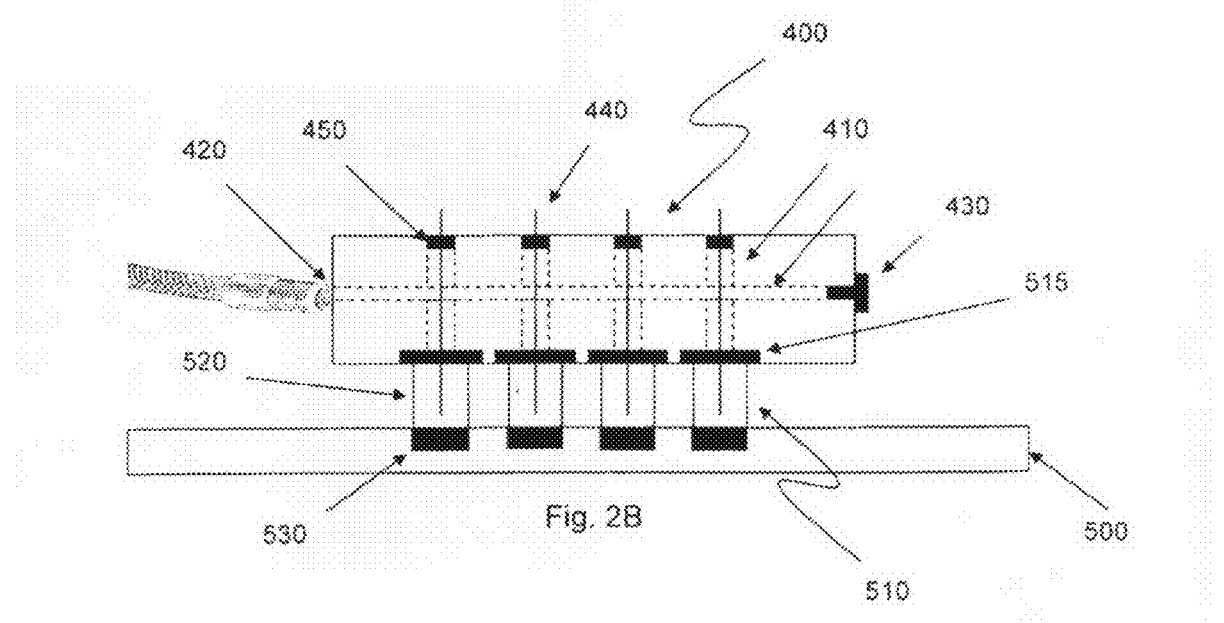

In another exemplary example, FIG. 2B shows a different type of wells where each well 510 has a tubular extension 520 in addition to a trench 530. The tubular extension 520 may serve to extend the liquid capacity of the trench 530 of the well. The tubular extensions 520 may have a volume of about 5 to 50 µl. However, as shown in FIG. 2A, the requisite volume needed for each well 510 may be provided by having a proper dimension entirely within the chip 500. Note that the manifold block 400 in this instance also shows electrodes 440 extending from the top of the block to the wells 510 through the interconnecting channels 410 for applying voltage. The well 510 may or may not have such an electrode, depending on the configuration and the need for it (FIG. 1 and FIG. 2A do not show any electrodes but could be provided in a similar manner). The hole created for inserting the electrodes 440 may be sealed by an epoxy glue 450. Also, in this example, the external port 420 is provided at the side of the manifold block 400 with a plug 430 at the opposite end to achieve a good seal.

FIG. 2C shows another embodiment of the invention. The components of this embodiment correspond to the components in FIG. 2B and have the same reference numbers as those in FIG. 2B. The main difference between the embodiments of FIGS. 2B and 2C is that the electrodes 440 in FIG. 2C are integrated into the manifold block 400 and, therefore, provided separately from the air ducts, i.e. the interconnecting channels 410. This configuration allows better electrode insulation and is amenable to sealing the wells more securely.

In the present embodiment of FIG. 2A, the capacity of each well 510 is about 25 µl. However, the capacity of each well can be appropriately designed to accommodate the sample size, which could vary from 0.1 nl to 500 µl, depending on the application. For conducting PCR, a range of 1 µl to 100 µl of sample size is common. Therefore, the wells used for the PCR chip 500 can be appropriately designed to have a capacity of, for example, 1µ to 100 µl to accommodate the PCR sample. The exemplary manifold block 400 has a channel width of about 1 mm and a depth of about 500 µm for the interconnecting channel. The channel dimensions are exemplary and may be varied according to design and targeted applications. The exemplary dimensions of the manifold block 400 are 37 mm×22.4 mm×12 mm. However, the dimension of the block should not be limited to the exemplary size described here. The dimension of the block itself may be varied, for example, according to the number of wells and/or their capacity size of a PCR chip.

An exemplary method for effecting PCR in FIG. 2A will now be described. Each PCR 25 µl reaction contained: 1×PCR buffer; 0.4 mM dNTP; 3 mM $MgCl_2$; 250 nM Forward primer CTCACCTATGTGTCGACCTG; 250 nM Reverse primer, GGTCGAGTACGCCTTCTTG; 1 µl BCG genomic DNA ($10^5$ copies); and 1 U rTaq DNA Polymerase.

A PCR reaction mixture of 25 µl was added into the PCR chip 500 from one well 510. The wells 510 were then overlaid optionally with approximately 1 µl of mineral oil. The manifold block 400, the O-rings 515, and the PCR chip 500 then were clamped together. In the assembled configuration, the wells 510 of the PCR chip 500 have common pressure passages by the interconnecting channels 410 within the manifold block 400 to balance any pressure differences and to allow for application of external pressure to the wells 510 to further suppress or prevent evaporation, condensation and unintended movement of liquid. The assembled manifold-PCR chip was then clamped on the top of the heating block of a thermal cycler 600 (see FIG. 2A). An external pressure of 30 psi was applied through the external port 420 at the top of the manifold block 400. A tube control reaction also was conducted to compare the DNA yields of the standard system and the manifold block-PCR chip assembly.

PCR was performed using the following cycle protocol: 1×96° C., 30 s; and 40×96° C., 15 s, 62° C., 15 s, and 72° C., 30 s. One µl of the product was analyzed on the Agilent Bioanalyzer using a DNA 1000 kit.

Figure 3A:
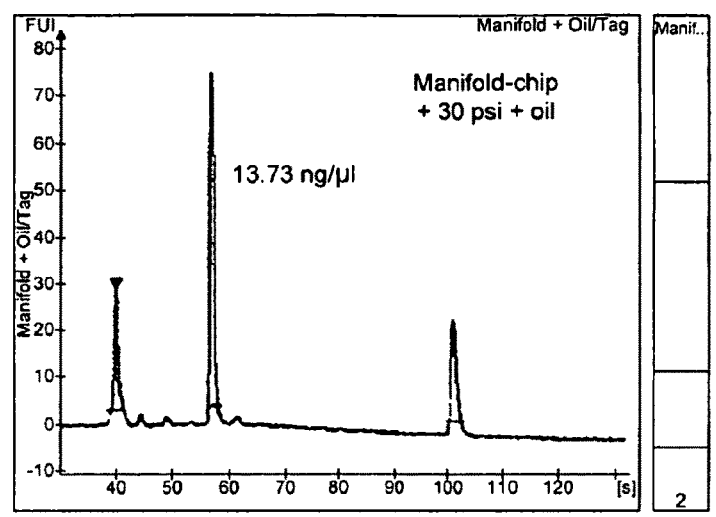
FIG. 3A shows exemplary measurements of results from an embodiment of the present invention and FIG. 3B shows a measurement of a control system.
Figure 3B:
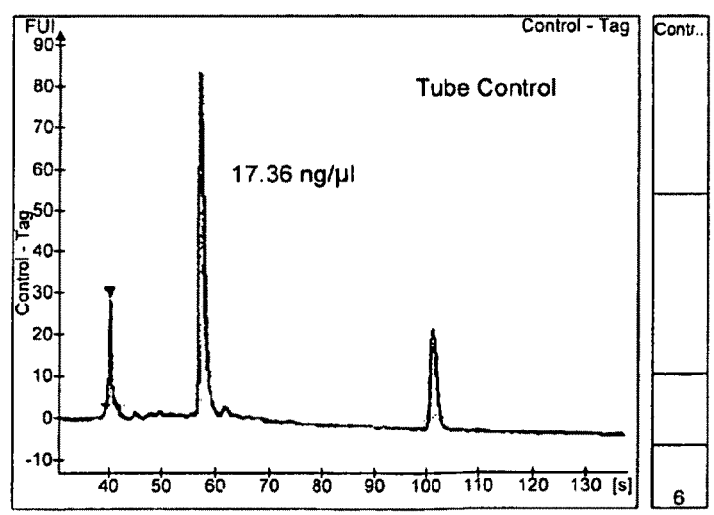

FIG. 3A shows the DNA product yield of 13.73 ng/µl for the manifold block-PCR chip assembly with mineral oil in the wells and 30 psi pressure applied to the assembly from an external source. FIG. 3B shows the DNA product yield of 17.36 ng/µl for the control reaction where the PCR reaction was conducted in a tube. Amplification of the 159-bp BCG target was successfully demonstrated with this setup, with the yield of 80% of the control tube reaction.

TABLE A

| Exp. No. | Experimental setup | Observation after 10 PCR cycles; total time of 26 minutes |
|---|---|---|
| 1 | Open chamber | wells dried out, no liquid |
| 2 | Manifold-closed-no pressure | Condensation in manifold channels, 50% of liquid in wells, bubbles |
| 3 | Manifold + 20 psi | Condensation in manifold channels, 80% of liquid in wells, no bubbles in bulk of liquid, large bubbles near each well |
| 4 | Manifold + 30 psi | condensation in manifold channels, 90% of liquid in wells, no bubbles in bulk of liquid, 1 large bubble near each well |
| 5 | Manifold + 30 psi + mineral oil | No condensation, 100% of liquid in wells |
| 6 | Manifold + 40 psi | Chip delaminated in one prototype |

A set of different experiments as summarized in Table A was further performed to show the effectiveness of the manifold block 400 in suppressing or preventing evaporation, condensation and unintended movement of liquid. For Experiments 1-6 described below, the PCR wells 510 were filled with a BSA solution, the cycle protocol was started to mimic the amplification reaction, and finally the amount of the BSA solution in the wells after 10 cycles (approximately 26 minutes) was determined.

Table A summarizes Experiments 1 to 6 and the corresponding results using the BSA solution. In Experiment 1, the PCR chip 500 was left open without the benefit of the manifold block 400. The result was that after the $10^{th}$ cycle, the wells dried out leaving no liquid.

In Experiment 2, the PCR chip 500 and the manifold block 400 were clamped together but no pressure was provided through the external port 420 during the PCR cycles. The result was that there was some condensation in the manifold interconnecting channels 410. Also, bubbles were observed, and only about 50% of the original solution remained.

In Experiment 3, the manifold block 400 and the PCR chip 500 were assembled and sealed, and this time 20 psi of pressure was applied through the external port 420 during the PCR cycles. There was still some condensation in the interconnecting channels 410 but no bubbles were observed in the solution in the wells 510. However, large bubbles were observed near each of the wells 510. About 80% of the original solution remained in the wells 510.

In Experiment 4, the manifold block 400 and the PCR chip 500 were assembled and sealed and 30 psi of pressure was applied through the external port 420 during the PCR cycles. In this case, some condensation in the interconnecting channels 410 and a large bubble near each of the wells 510 were observed. However, approximately 90% of the original solution remained in the wells 510.

In Experiment 5, mineral oil was applied to the wells, and the manifold block 400 and the PCR chip 500 were assembled and sealed. And approximately, 30 psi of pressure was applied through the external port 420 during the PCR cycles. This time, there was no condensation and approximately 100% of the solution remained in the wells.

In Experiment 6, after the assembly of the manifold block 400 and the PCR chip 500, 40 psi of pressure was applied through the external port 420 during the PCR cycles. For this particular assembly, the pressure delaminated the chip. However, a stronger construction of the chip 500 should make the assembly withstand the higher pressure and such a construction is not beyond the scope of the invention.

Experiments 1 to 5 showed that Manifold block helped to suppress or prevent evaporation, condensation, and unintended movement of liquid within the chip. Although, mineral oil may further help suppress evaporation in the well, it may not be necessary as Experiment 8 below shows.

TABLE B

| 7 | Manifold + 40 psi | no chip delamination with a chip with strengthened lamination construction |
|---|---|---|
| 8 | Manifold + 35 psi | essentially 100% of liquid in chamber after 40 cycles of PCR, total time 1 hour. No mineral oil in wells. |

Table B shows a summary of two additional experiments with the manifold block 400 and a PCR-CE chip similar to the chip 500 (similar to what is shown in FIG. 2B) but made to have a stronger lamination construction to withstand higher pressure. For each experiment, 40 cycles of PCR were run for a total duration of approximately one hour.

In Experiment 7, it was verified that the stronger laminated construction of the chip was able to withstand the pressure of 40 psi. No delamination occurred at this pressure. With a stronger material and better reinforced construction, the chip should be able to withstand a much higher pressure.

Figure 4:
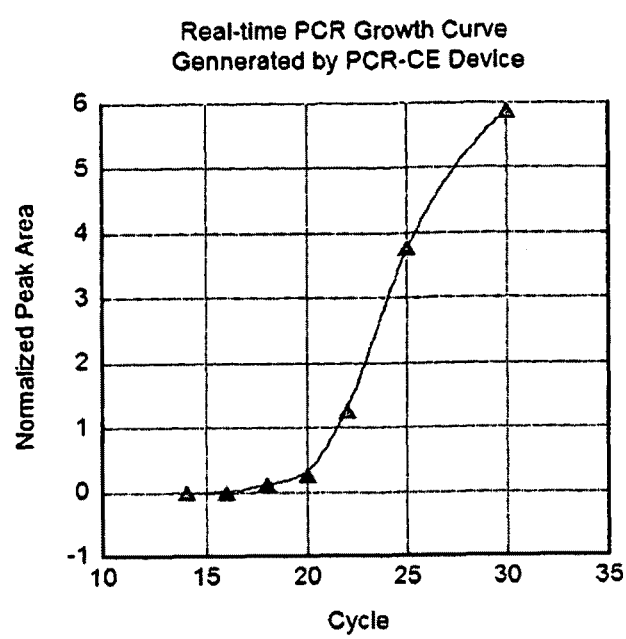
FIG. 4 is a PCR growth curve.
Figure 5:
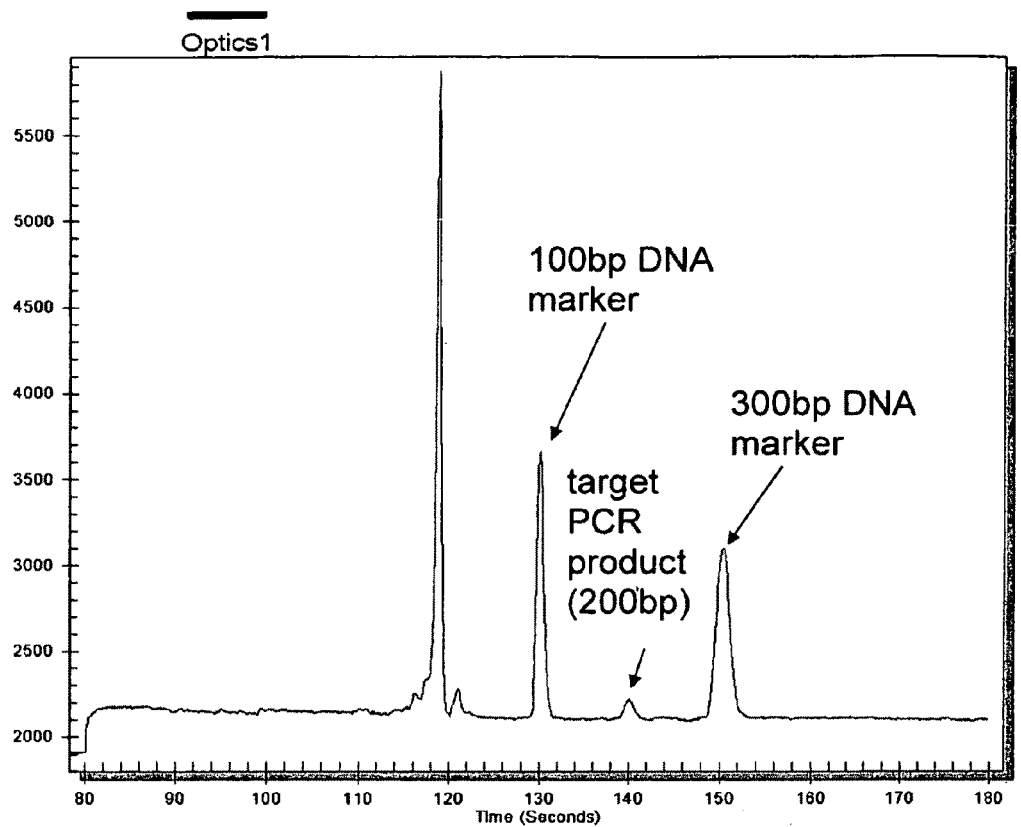
FIG. 5 is an electropherogram of capillary electrophoresis (CE) separation at $18^{th}$ cycle when the PCR target product starts to be detectable.

In Experiment 8, the result of a real time 40-cycle PCR-CE assay of FIG. 4 is presented. The CE separation channels of the PCR-CE chip were filled with gel matrix and 28 ul of a PCR reaction mix was loaded on to the chip chamber. After assembling the manifold block 400 and the PCR-CE chip and placing it on a thermal cycling heater, 35 psi of pressure was applied through the external port 420 during the PCR cycles. Real time amplification was successfully detected. By applying a voltage between the wells at cycles 14, 16, 18, 20, 22, 25, and 30, PCR product samples from the chamber were induced to migrate into the CE separation channel for analysis. The peak area of the PCR product was normalized using an internal marker (100 bp DNA) in the PCR mix and plotted against the cycle number to generate the real time PCR product growth curve, as shown in FIG. 4. FIG. 5 shows an electropherogram of CE separation at the $18^{th}$ cycle of the same real time PCR-CE assay above. It demonstrated that the target PCR product sample (200 bp) starts to be detectable at or about the $18^{th}$ PCR cycle. Evaporation was substantially prevented such that essentially 100% of liquid remained in the chamber after 40 cycles of PCR. The total time was 1 hour and no mineral oil was used in the wells. Mineral oil was not used in this example to show that evaporation can be essentially prevented without its use.

Evaporation of reaction mix from PCR wells was suppressed by using a combination of manifold and an applied external pressure up to 30 psi. Adding mineral oil to the well after the solution is added may further help reduce evaporation. But as shown in Experiment 8, the standard practice of dropping one drop of mineral oil on top of the well to prevent evaporation at high temperatures can be obviated with the device of the present embodiment.

Figure 6:
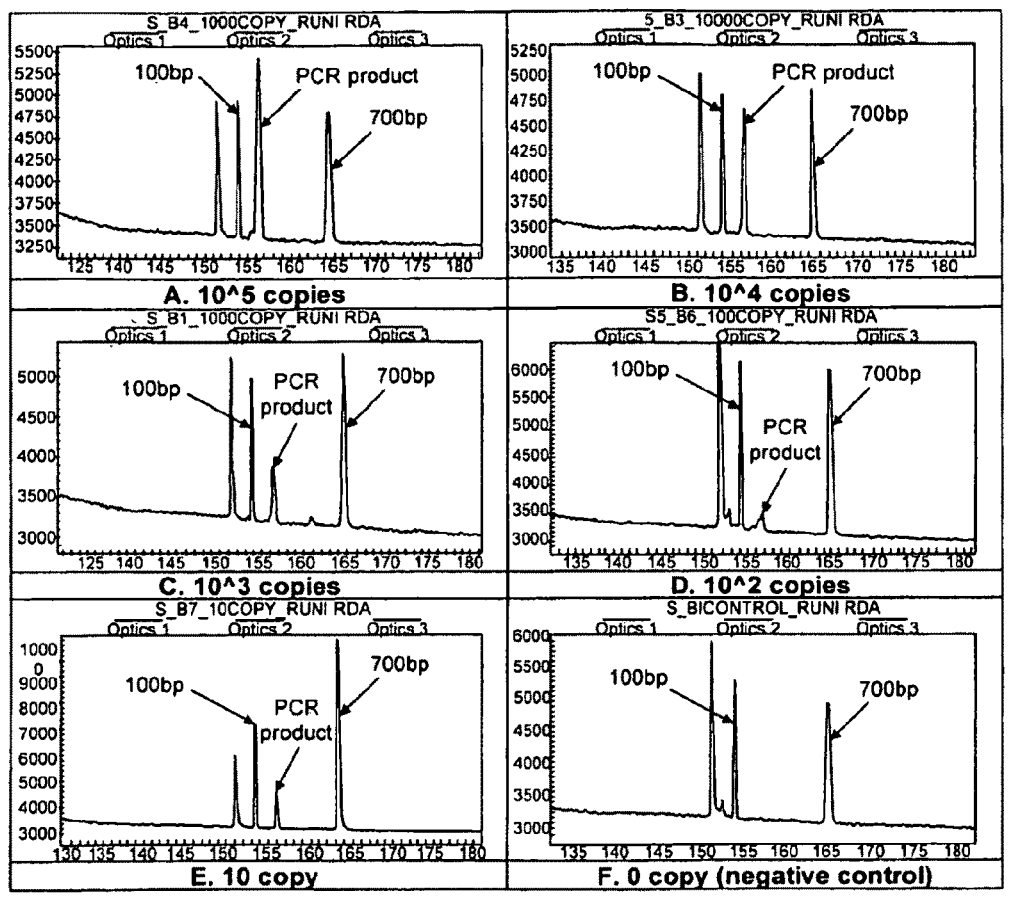
FIG. 6 provides electropherogram of CE separation results at from zero copy to $10^5$ copies.

Additional experiments were performed with the configuration similar to one shown in FIG. 2B. The methods and protocols are basically the same as reported in the previous experiments. The results of performing the 40 PCR cycle end-point CE assay at 35 psi with no application of oil are presented in graphs in FIG. 6. The internal reference markers are indicated as 100 bp and 700 bp. The actual PCR products are positioned between the 100 bp and 700 bp internal markers. The electropherograms A to F provide the results of detecting the DNA target copy range from $10^5$ to 10 per assay. In all of the experiments, there were no appreciable loss of liquid with the application of the pressure manifold device to keep equal pressure for all of the wells and channels.

Figure 7:
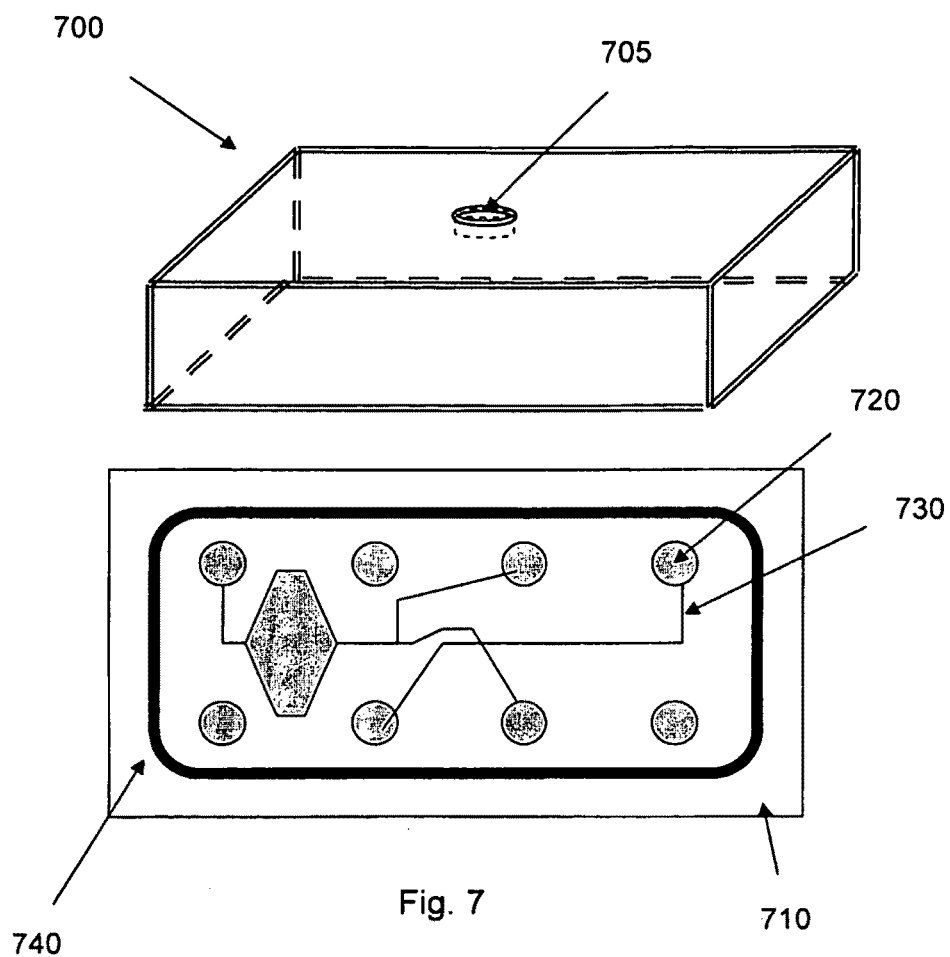
FIG. 7 is another embodiment of a device of the present invention.
Figure 8:
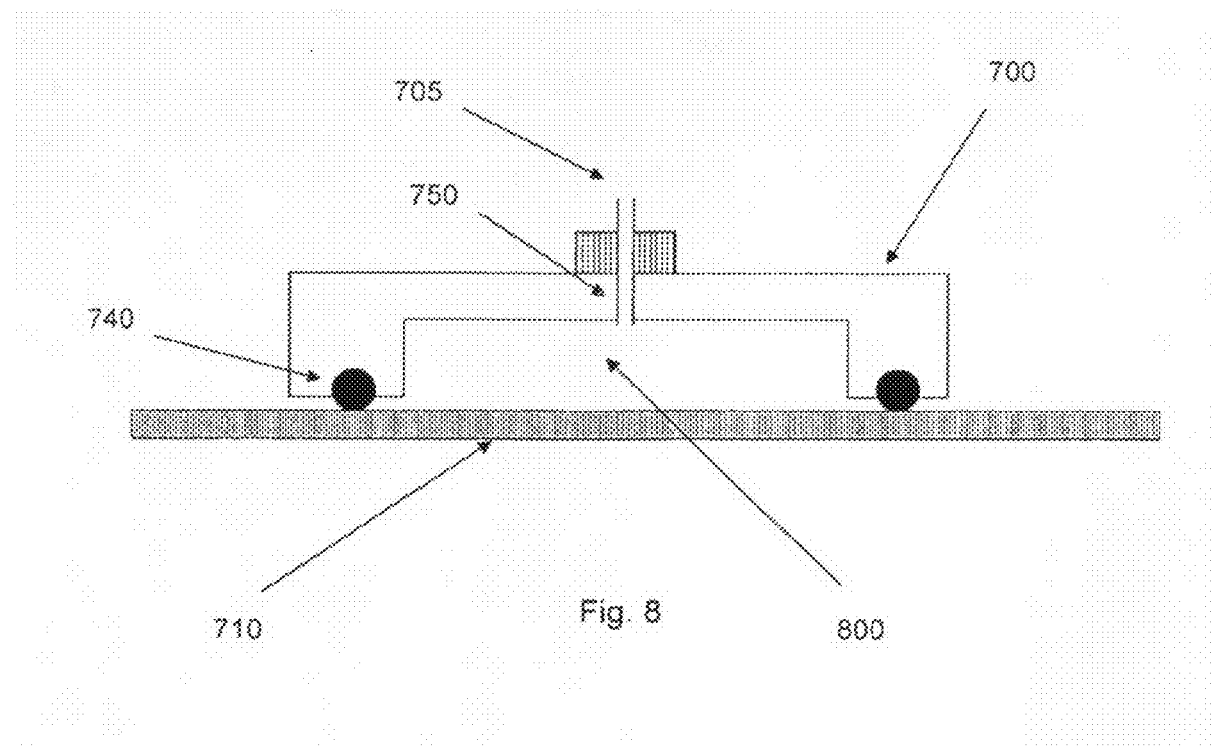
FIG. 8 is still another embodiment of a device of the present invention.

Another embodiment of this invention is shown in FIG. 7. A pressure manifold block 700 in this case is a block with a single channel for being disposed over a microfluidic PCR-CE chip 710. An external pressure port 705 is provided at the top of the pressure manifold block 700. The manifold block 700 functions as a lid to be disposed over all of microfluidic wells 720 and separation channels 730 of the chip 710 to minimize or suppress pressure differences generated between the wells 720 during PCR thermal cycling. A gasket 740 such as a silicone O-ring surrounds all the wells 720 and the separation channels 730 and is sandwiched between the manifold block 700 and the PCR-CE microfluidic chip 710. The manifold block 700 may be a solid block such that a common gap space is formed by the gasket 740 between the block 700 and the chip 710. Alternatively, as seen in FIG. 8, the manifold block 700 may have a sealed cavity 800 formed between the chip 710 and the block 700. Referring to both FIGS. 7 and 8, the external pressure port 705 leads to the cavity or the gap through an air passage (a single channel) 750. The assembled manifold gaskets-PCR-CE chip is then clamped together to ensure complete sealing. By applying a regulated external pressure through the external pressure port 705 on the manifold block 700 to equalize the pressure above all the wells 720 and the separation channels 730, evaporation, condensation, and unintended movement of solutions can be suppressed or prevented within the chip 710.

Figure 9:
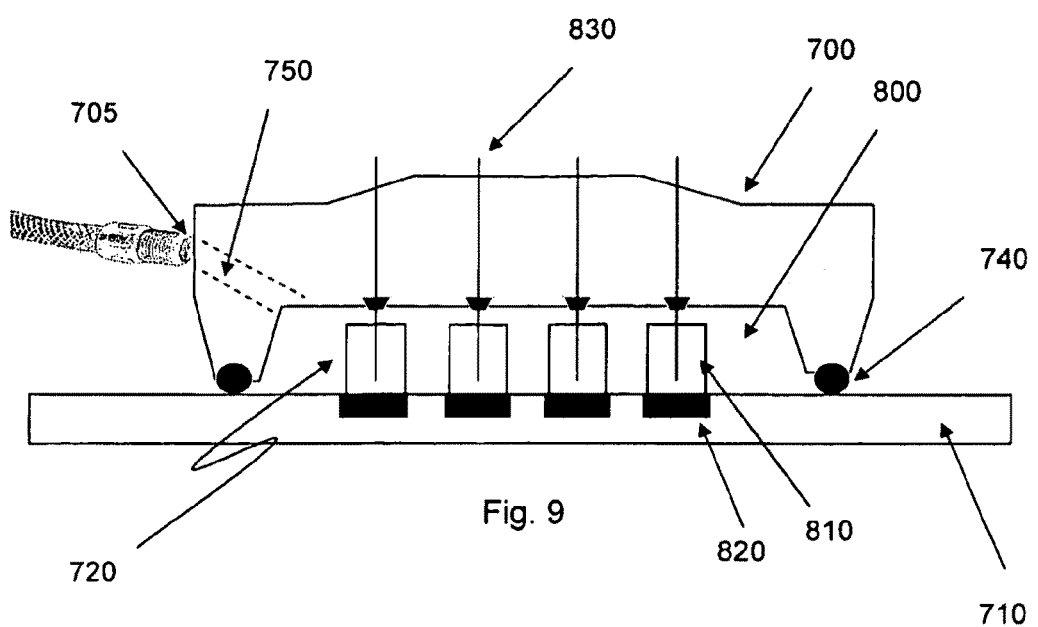
FIG. 9 is another embodiment of a device of the present invention.

FIG. 9 shows another exemplary embodiment where the presence of the cavity 800 between the chip 710 and the manifold block 700 and sealed by the gasket 740 allows for the accommodation of tubular extensions 810 of the wells 720. The wells 720 are made of both trenches 820 and the tubular extensions 810. The dimensions of the manifold block 700 may be large enough to be placed over the chip 710 and may have a cavity of large enough size to clear the tubular extensions 810. FIG. 9 shows the external pressure port 705 and the air passage 750 at the side of the manifold block 700 but it can be anywhere including the top. Electrodes 830 are shown for each of the wells 720 in this embodiment but not every well may require an electrode, depending on the design of the chip 710. Other figures such as FIGS. 7 and 8 do not show electrodes but these were left out purely to simplify the viewing of the manifold block.

Figure 10:
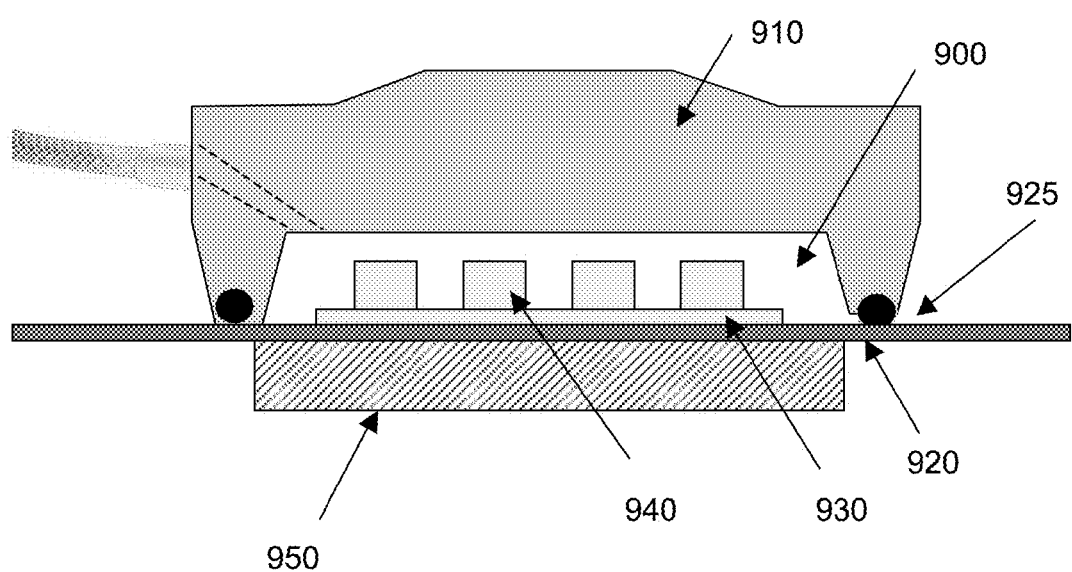
FIG. 10 is another embodiment of a device of the present invention.

FIG. 10 shows another exemplary embodiment where a sealed cavity 900 formed between a manifold block 910 and a base 920 is hermetically sealed by a gasket 925 around the periphery where the manifold block 910 contacts the base 920. A chip 930 with wells (tubular extensions) 940 and channels (not shown) are completely enclosed within the cavity 900. Also, in this embodiment, the electrodes for providing voltages to the wells 940 are completely embedded in or printed on the chip 930 so no electrodes are needed to pierce the manifold block to get to the wells. A thermal cycler 950 may be attached to or integrated into the bottom of the base 920. The base 920 may be made of metal such as copper or aluminum, or it may be made of plastic material that can suitably conduct heat from the thermocycler 950 to the chip 930. The shape of the base 920 is suitably sized to support both the chip 930 and the contact of the manifold block 910. The advantage of this configuration is that because the manifold block 910 completely encloses the chip 930 itself, there is no added contact pressure on the chip 930 to impart stress. Furthermore, the lamination of the chip 930 experiences only the internal equal air pressure of the cavity 900 and no pressure differences of the internal cavity pressure and the external air pressure like the chip 710 of FIG. 9. Thus, according to this configuration, the chip 930 is less prone to delamination, leakage, or other type of damages. Also, the total enclosure of the chip 930 assures that pressure is even throughout all the wells and channels.

Before or after being pressurized, the manifold block as provided in any of the embodiments can also be heated by convection (e.g. blowing hot air) or by conduction (e.g. applying resistive heating) to further prevent condensation from forming within the cavity created by the manifold block.

Applications of the manifold block are not limited to use with a PCR chip. The present embodiments of the manifold blocks are shown with respect to their use with PCR-CE chips but the manifold block may also be used to equalize pressure in a microfluidic device with wells for conducting chemical or biological reactions that do not involve PCR.

Also, an external pressure source supplying pressured air to a microfluidic device may be closed to maintain pressure within the microfluidic device made of inter alia a manifold block and a microfluidic chip. For example, a tubing supplying high pressure air from the external pressure source may have a clamping mechanism or a similar mechanism to cut off air and to maintain pressure in the manifold block-microfluidic chip device. The tubing may also be detachable near the clamping mechanism so that the manifold block and the chip as a closed system may be portable while still maintaining high pressure.

Alternatively, a manifold block in conjunction with a microfluidic chip may be configured as a closed system, that is, a system with external openings that are sufficiently sealed or a system without any external openings. In this system, the pressure inside the manifold may be increased internally by, for example, heating selectively one well with low boiling point liquid or placing dry ice in the well. The equalized pressure within the manifold block in this arrangement would function to suppress or prevent evaporation and condensation of liquid in the remaining wells and unintended movement of liquid in the channels.

A low cost, disposable device with a manifold block is presented. The manifold block is sealed over a PCR chip to suppress or prevent evaporation, condensation, and unintended movement of liquid therein because of pressure differences in PCR chip channels during PCR cycles. The device is used in the microfluidic regime but it can also be use in a more macroscopic scale.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method of equalizing pressure over all wells of a microfluidic device that are interconnected by microfluidic channels, the method comprising:

providing the microfluidic device comprising a plurality of wells that are interconnected by microfluidic channels, wherein the plurality of wells comprise all the wells that the microfluidic channels interconnect, loaded with a liquid in the interconnected microfluidic channels;

disposing over the plurality of wells a gas manifold block, the gas manifold block comprising a first surface having at least one opening therein, a port, and a channel within the gas manifold block connecting the port to each of the at least one opening in the first surface, wherein the at least one opening in the first surface covers the plurality of wells of the microfluidic device such that the gas manifold block and wells form an enclosed volume filled with gas that communicates with the external environment only via the port; and pressurizing the enclosed volume over the plurality of wells by supplying pressurized gas through the port on the gas manifold block, whereby the pressure over the plurality of wells is equalized.

2. The method of claim 1, further comprising adding mineral oil to the plurality of wells before disposing the manifold block over the plurality of wells.

3. The method of claim 1 or 2, wherein the closed system over the plurality of wells is pressurized to at least 10 psi.

4. The method of claim 1, wherein the gas manifold block comprises a plurality of openings in the first surface, wherein the openings each mark the ends of channels of an interconnecting channel system within the gas manifold block that connects to the port, and wherein the plurality of openings align with the plurality of wells of the microfluidic device when the manifold block is disposed thereon.

5. The method of claim 4, wherein a gasket is disposed between the gas manifold block and the perimeter of each well.

6. The method of claim 1, wherein the opening in the first surface of the gas manifold block defines a cavity, and wherein when the manifold block is disposed over the plurality of wells, the plurality of wells lie within the cavity.

7. The method of claim 4, 5, or 6, further comprising adding mineral oil to the wells before disposing the gas manifold block over the plurality of wells.

8. A system for equalizing a positive gas pressure over wells of a microfluidic device, the system comprising:

the microfluidic device comprising a plurality of wells that are interconnected by microfluidic channels, wherein the plurality of wells comprise all the wells that the microfluidic channels interconnect;

a gas manifold block comprising a first surface having at least one opening therein, a port on the outer surface of the gas manifold block that is not within the at least one opening, and a channel within the gas manifold block connecting the port to each of the at least one opening in the first surface, wherein the at least one opening in the first surface of the gas manifold block is disposed over the plurality of wells of the microfluidic device such that the gas manifold block and wells form an enclosed volume filled with gas that communicates with the external environment only via the port of the gas manifold block; and a source of pressurized as connected to the port on the gas manifold block.

9. The system of claim 8, wherein the source of pressurized gas can supply gas at least 10 psi.

10. The system of claim 8, further comprising at least two electrodes, each positioned in a different well.

11. The system of claim 10, wherein the electrodes are printed on the microfluidic device.

12. The system of claim 8, wherein the gas manifold block comprises a plurality of openings in the first surface, wherein the openings each mark the ends of channels of an interconnecting channel system within the gas manifold block that connects to the port, and wherein the plurality of openings align with the plurality of wells of the microfluidic device such that the gas manifold block and wells form a closed system.

13. The system of claim 12, wherein a gasket is disposed between the gas manifold block and the perimeter of each well.

14. The system of claim 8, wherein the opening in the first surface of the gas manifold block is a cavity, wherein when the gas manifold block is disposed over the plurality of wells, the plurality of wells lie within the cavity.

15. The system of claim 12, 13, or 14, wherein each well has a tubular extension.

16. The system of claim 8, wherein the microfluidic device further comprises a reaction chamber and an electrophoresis channel in fluidic communication with the plurality of wells.

17. The system of claim 16, further comprising a thermal cycler heat block in thermal contact with the microfluidic device, and wherein the microfluidic device is configured (i) to perform a polymerase chain reaction to thereby produce a reaction product and (ii) to inject portions of the reaction product into an electrophoresis channel within the microfluidic device.

18. A system for equalizing a positive gas pressure over wells of a microfluidic device, the system comprising:

the microfluidic device comprising a plurality of wells that are interconnected by microfluidic channels, wherein the plurality of wells comprise all the wells that the microfluidic channels interconnect;

means for sealing off the plurality of wells interconnected by microfluidic channels from the external environment, wherein said means is filled with gas; and means for pressurizing the gas within said means for sealing off the plurality of wells interconnected by microfluidic channels from the external environment;

thereby providing a system for equalizing a positive gas pressure over the plurality of wells interconnected by microfluidic channels.

* * * * *